United States Patent [19]

Jefferies et al.

[11] Patent Number: 4,772,284
[45] Date of Patent: Sep. 20, 1988

[54] BREAST PROSTHESIS WITH IMPROVED BIOCOMPATIBILITY AND METHOD OF MAKING THE SAME

[75] Inventors: Steven R. Jefferies; Robert J. Spence, both of Baltimore, Md.

[73] Assignee: Collagenix Corporation, Washington, D.C.

[21] Appl. No.: 845,125

[22] Filed: Mar. 27, 1986

[51] Int. Cl.$^4$ .............................................. A61F 2/52
[52] U.S. Cl. .................... 623/8; 128/DIG. 8
[58] Field of Search ........................ 623/4–8, 623/66; 128/DIG. 8

[56] References Cited

U.S. PATENT DOCUMENTS 4,597,762 7/1986 Walter et al. ...................... 623/8 X
4,648,880 3/1987 Brauman ............................... 623/8

Primary Examiner—Richard J. Apley
Assistant Examiner—Alan W. Cannon
Attorney, Agent, or Firm—Eric P. Schellin

[57] ABSTRACT

A single lumen implantable and biocompatible breast prosthesis composed of an outer membrane of silastic, medical grade silicone, and an inner filling material selected from the group consisting of purified reconstituted collagen gel and a purified gel of poly-alpha amino acid homopolymers or random copolymers having a molecular weight of from 5,000 to 400,000. The purified reconstituted collagen gel has a collagen concentration of from 20 to 100 milligrams per milliliter of gel.

3 Claims, No Drawings

BREAST PROSTHESIS WITH IMPROVED BIOCOMPATIBILITY AND METHOD OF MAKING THE SAME

BACKGROUND OF THE INVENTION

The reconstruction of the breast following ablative surgery has become an increasingly frequent surgical procedure. The development and use of silicone-gel and saline-filled silastic implants have contributed to the increased frequency of this procedure. Thickening and contracture of the fibrous capsule surrounding the silastic implant, however, remains a major post-surgical problem. Animal studies, as well as histologic evaluation of human capsule segments, have revealed the nature of this fibroproliferative response. Leakage or "bleeding" of silicone gel from silastic breast implants appears to be a major cause of this inflammatory response, which ultimately results in a constrictive fibrosis surrounding the silicone-gel implant. The use of "double-lumen" prostheses, with the outer chamber containing saline, decreases the inflammatory response initially but does not eliminate the ultimate fibroproliferative response. This application describes breast prostheses which contain less reactive, more biocompatible filling substances. The use of such breast prostheses will limit and control thickening and contracture of the fibrous capsule surrounding the prosthesis.

SUMMARY OF THE INVENTION

Silastic and silicone bag prostheses have been filled with reconstituted collagen gels and gels formed from poly-apha-amino acids. These prostheses may consist of single or multiple lumen prostheses. Double or multiple lumen prostheses may contain a central filling material of either saline or silicone gel surrounded by an outer chamber of reconstituted collagen gel or a polyamino acid gel material. Alternatively, the double lumen prostheses may contain an inner chamber filled with purified collagen gel or a polyamino acid gel surrounded by an outer sealed chamber containing saline.

Other implantable bioprostheses can be formulated by placing reconstituted collagen membranes and sponge-materials between two sheets or membranes of a synthetic resorbable or nonresorbable material. These laminar biomaterials can also be utilized as wound dressings or wound coverings in certain circumstances.

EXAMPLE 1

Single lumen silastic or curved membrane bags can be filled with a purified, sterilized, reconstituted collagen gel and sealed to maintain the integrity of this collagen-gel breast prosthesis. The collagen concentration of the collagen-gel used can vary anywhere from 20 mg per milliliter to 100 mg per milliliter. Glutaraldehyde, in concentrations ranging from 0.005% to 1%, may be added to the collagen gel to crosslink the matrix, thereby decreasing the solubility of the matrix within the membrane structure. Additionally, antibiotics, such as tetracycline, can be dispersed within the collagen gel matrix.

EXAMPLE 2

Single lumen silastic or cured silicone membrane bags can be filled with gel composed of a naturally occurring alpha-amino acid, for example, poly-L-lysine. Homopolymers of polyamino acids such as poly-L-Lysine, poly-O-Acetyl-L-Hydroxyproline, poly-O-Acetyl-L-Serine, poly-L-Alanine, Poly-L-Arginine, poly-L-Aspartic acid, poly-L-Asparagine, or any of the other D or L polymers of one of the twenty naturally occurring amino acids. Molecular weights of these polyamino acid polymers can vary anywhere from 5,000 to 400,000. In addition, randon co-polymers of L-amino acids can be utilized.

As with reconstituted collagen gels, homopolymer gels or random co-polymer gels can be crosslinked with chemical crosslinking agents such as glutaraldehyde or hexamethylene disocynate. Concentrations of these agents can vary anywhere from 0.05 to 5 percent by volume in the gel itself.

EXAMPLE 3

A double lumen prosthesis can be constructed from a sphere within a sphere structure made from an acceptable, impermeable, biocompatible, polymer. Current breast prostheses are fabricated from silastic or silicone membranes. The inner sphere or chamber of this double lumen prosthesis can contain:

(a) sterile normal, phosphate-buffered saline,
(b) purified, sterile reconstituted collagen with a concentration of from 20 mg to 100 mg per milliliter, with or without the presence of a chemical crosslinking agent,
(c) purified, sterile gel of polyamino acid homopolymers or random copolymers, with or without the presence of a chemical crosslinking agent.

The outer sphere or chamber of this double lumen prosthesis can contain:

(a) sterile normal, phosphate-buffered saline,
(b) purified, sterile reconstituted collagen with a concentration of from 20 mg to 100 mg per milliliter, with or without the presence of a chemical crosslinking agent.
(c) purified, sterile gel of polyaamino acid homopolymers or random copolymers, with or without the presence of a chemical crosslinking agent.

EXAMPLE 4

A more resilient bioprosthesis or wound dressing may be fabricated using a similar concept as that applied in Examples 1, 2 and 3. Here, a reconstituted collagen sponge material or a collagen membrane material is sandwiched between two layers of a synthetic polymer membrane material. The collagen layer can contain a medication for topical application. The porous structure of the synthetic polymer layer can control the release of the drug or any solubilized collagen to the wound site. Alternatively, the synthetic polymer layers can be of a resorbable nature, allowing gradual exposure of the collagen membrane to the wound environment. A membrane prepared from a crosslinked polyamino acid polymer can be substituted for any of the described layers of this prosthesis.

What is claimed is:

1. A single lumen biocompatible implantable breast prosthesis composed of an outer membrane of silastic, medical-grade silicone, and an inner filling material selected from the group consisting of (a) purified, reconstituted collagen gel, wherein said collagen has a concentration of from 20 to 100 milligrams per millimeter of gel, and (b) a purified gel of poly-alpha amino acid homopolymers or random copolymers having a molecular weight of from 5,000 to 400,000 whereby the outer membrane, when filled with the inner filling material takes on the configuration of a natural human female breast.

2. The prosthesis of claim 1, wherein said collagen gel is crosslinked with glutaraldehyde or hemamethylene diisocyanate at a concentration of from 0.005% to 5% by volume.

3. The prosthesis of claim 1, wherein the gel in (b) is crosslined with a chemical crosslinking agent.

* * * * *